United States Patent [19]

Matsuura et al.

[11] Patent Number: 4,736,734
[45] Date of Patent: Apr. 12, 1988

[54] ENDOSCOPE WITH VARIABLE ILLUMINATION ANGLE

[75] Inventors: Nobuyuki Matsuura; Masahide Kanno, both of Tokyo; Haruo Takeuchi, Ina; Akibumi Ishikawa, Hachioji, all of Japan

[73] Assignee: Olympus Optical Co., Ltd., Japan

[21] Appl. No.: 881,816

[22] Filed: Jul. 3, 1986

[30] Foreign Application Priority Data

Jul. 12, 1985 [JP] Japan .................. 60-153573

[51] Int. Cl.[4] ............................. A61B 1/06
[52] U.S. Cl. .................... 128/6; 350/96.26; 358/98
[58] Field of Search ............ 128/4, 6; 350/96.26; 358/98

[56] References Cited

U.S. PATENT DOCUMENTS

| | | | |
|---|---|---|---|
| 3,090,378 | 5/1963 | Sheldon et al. | 128/4 |
| 3,178,994 | 4/1965 | Lang | 128/6 X |
| 4,076,018 | 2/1978 | Heckele | 128/6 |
| 4,390,012 | 6/1983 | Mizumoto | 128/4 |
| 4,452,236 | 6/1984 | Utsugi | 128/4 |

Primary Examiner—William H. Grieb

[57] ABSTRACT

An endoscope having a light source unit, a light guide fiber for guiding illumination light from the light source unit to the distal end in the inserting section of the endoscope main body, an optical system provided in the distal end for guiding the illumination light transmitted via the light guide fiber to an object, and a solid-state image pickup element incorporated in the distal end. A lens of the optical system is supported by a frame movable along an optical axis thereof. The frame is moved along the optical axis by a wire operating device provided in a control section of the endoscope main body in order to vary the angle of view of the optical system, i.e., the illuminating angle of the illuminating light. The image obtained by the solid-state image pickup element is enlarged by an image enlargement processor in accordance with the angle of view of the optical system, and is displayed. The image enlargement processor has a first frame memory and a second frame memory. The first frame memory receives only a predetermined horizontal scanning line components of the image which corresponds to the angle of view, and enlarges the image along the horizontal direction. The second frame memory receives only a predetermined component of each scanning line component read out from the first frame memory which corresponds to the angle of view, and enlarges the image along the vertical direction.

11 Claims, 6 Drawing Sheets

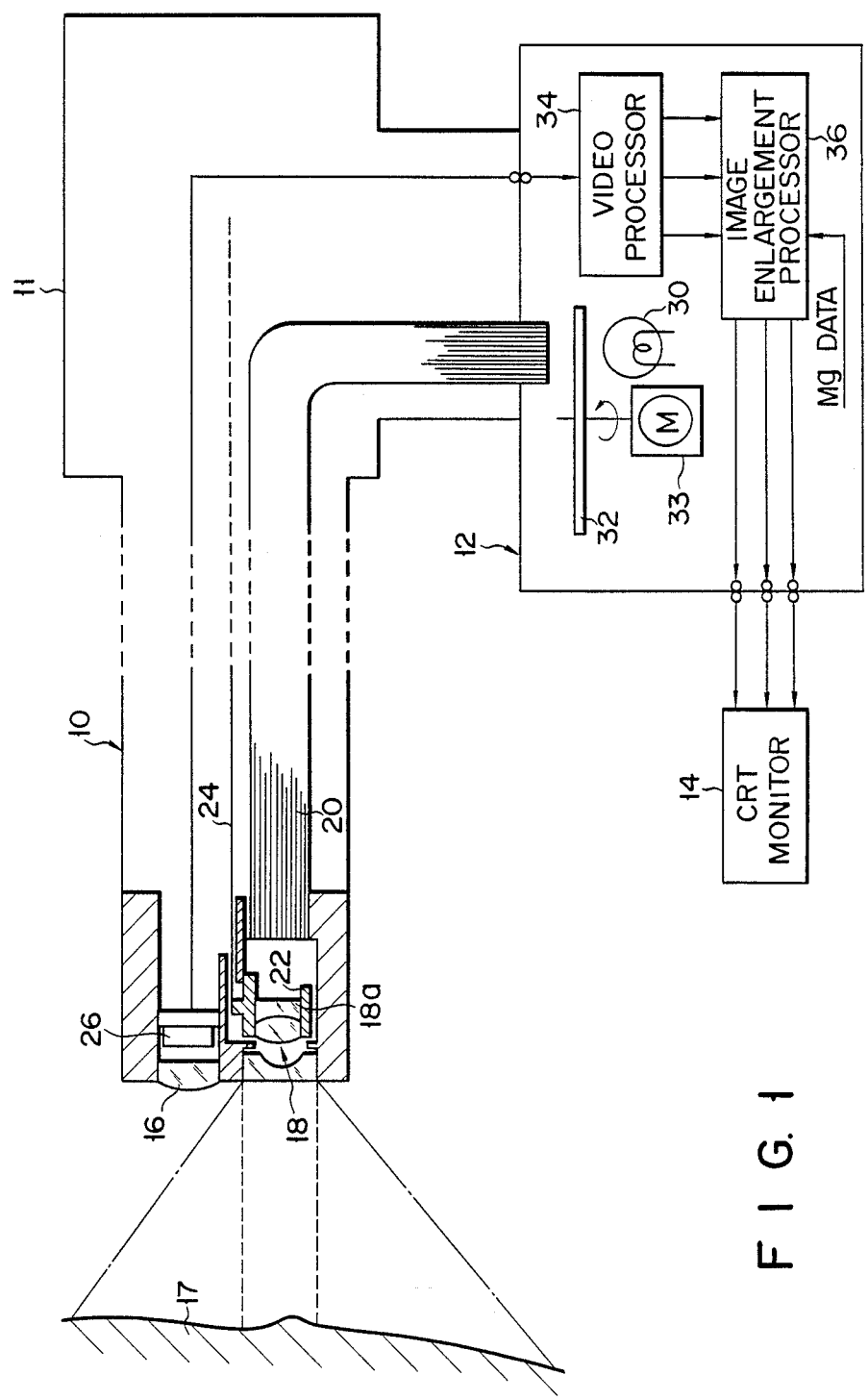
F I G. 1

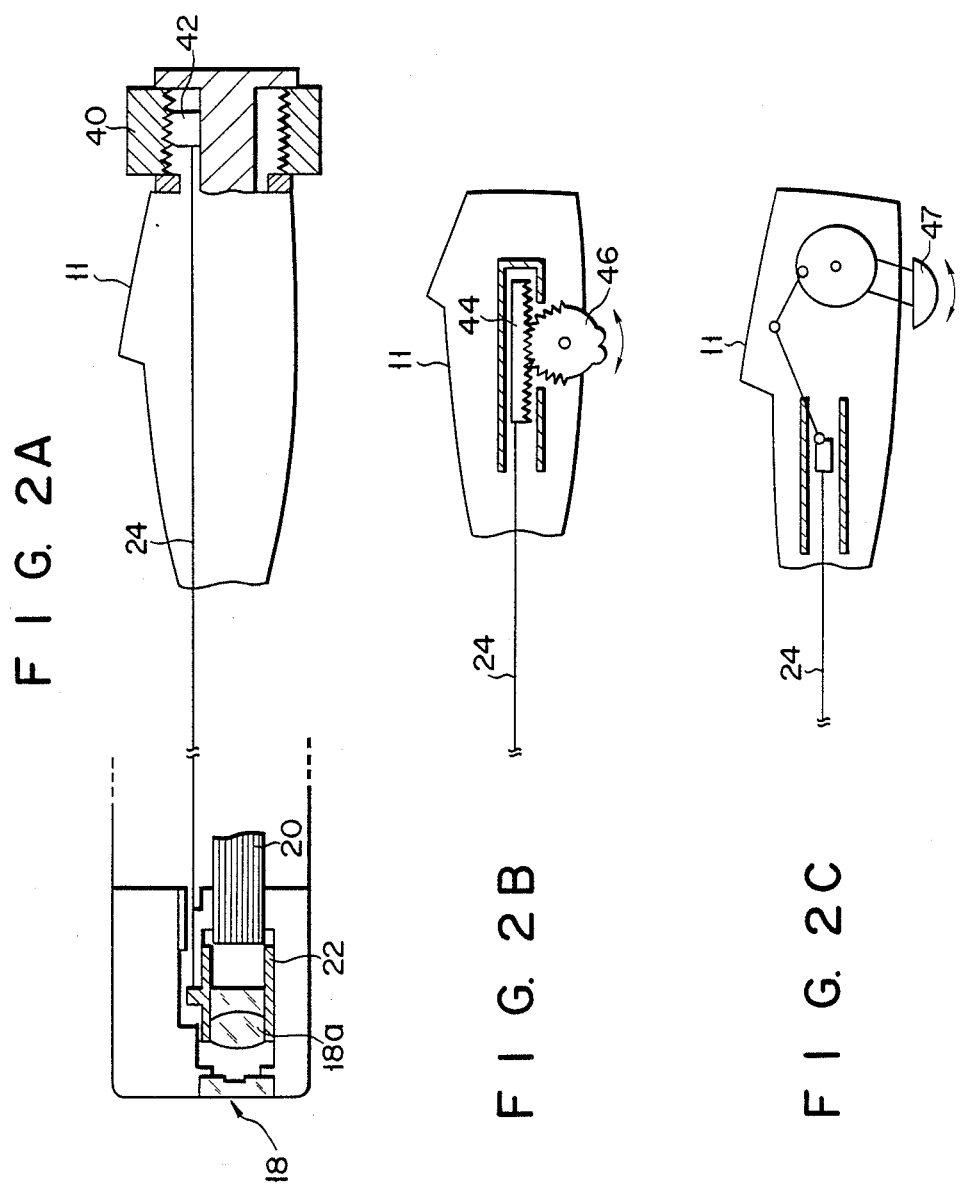

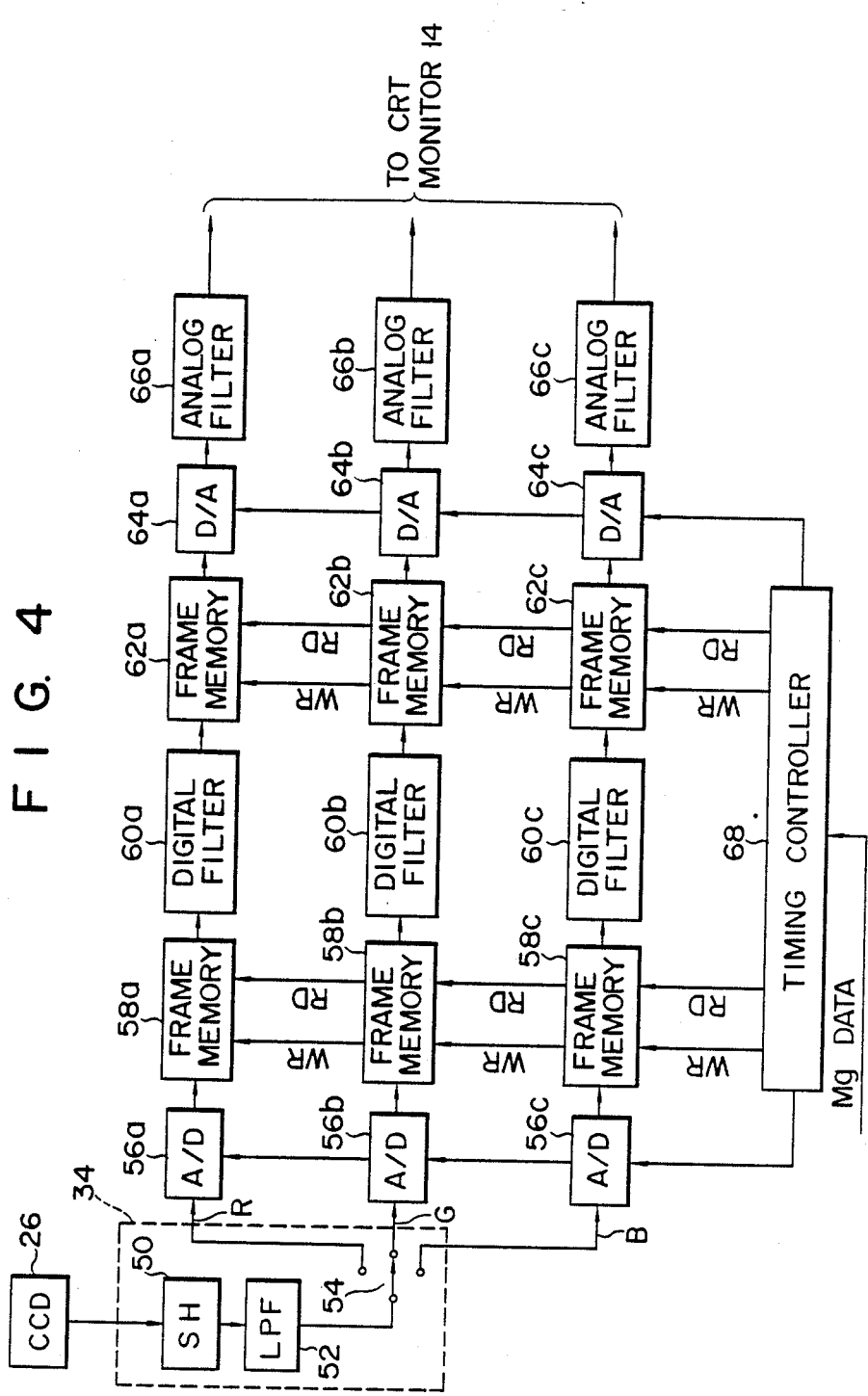

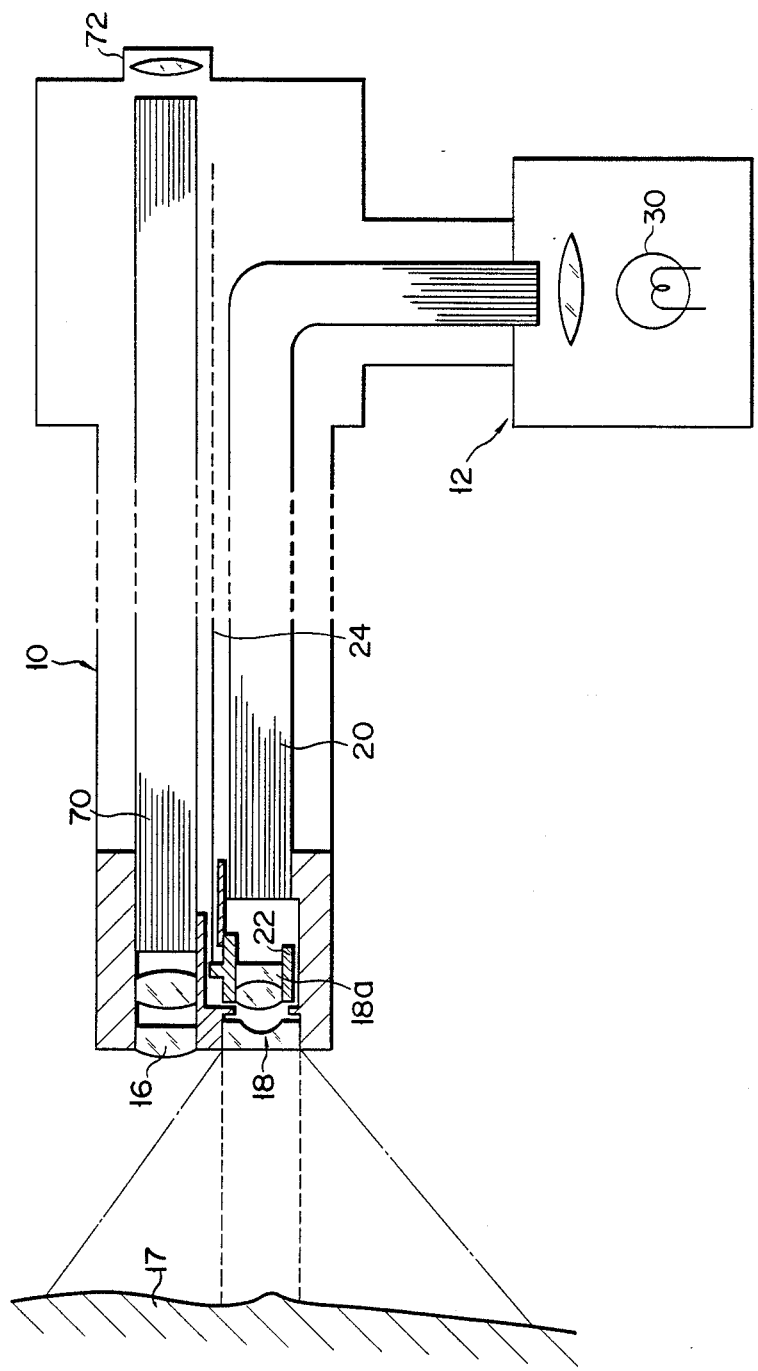

ENDOSCOPE WITH VARIABLE ILLUMINATION ANGLE

BACKGROUND OF THE INVENTION

The present invention relates to an endoscope and, more particularly, to an endoscope requiring a light source when an object under examination is in shadow or is completely dark.

When a body cavity or a narrow body passage is observed with an endoscope, an object therein is in shadow or is completely dark. A light source for illuminating the object is thus required. There are two types of light sources, i.e., an external light source type wherein the light source is provided outside the endoscope main body, and an internal light source type wherein the light source is incorporated in the distal end of the inserting section of the endoscope.

In the external light source type endoscope, a light source unit is provided outside the endoscope main body. The light emitted from the light source unit is transmitted to the distal end of the inserting section of the endoscope through an optical fiber bundle called a light guide, and irradiates the object through an illumination optical system. However, the illumination light emitted from the light source unit is attenuated during transmission in the light guide. Therefore, the intensity of the illumination light depends on the illuminance of the light source lamp in the light source unit and the light transmissivity of the light guide.

An endoscope is often inserted in a narrow body portion as described above. If the number of the optical fibers is increased to obtain a light guide with a larger diameter, in the interest of improving the light transmissivity of the light guide, the diameter of the inserting section is undesirably increased. For this reason, in order to increase the intensity of the illumination light, a light source lamp with a higher illuminance must be employed in the light source unit. This leads to an increase in the size of the light source lamp. The size of the light source unit itself must be increased to avoid adverse effects caused by heat generation, resulting in high cost.

In the internal light source type endoscope, when the intensity of the illumination light is to be increased, a light source lamp with a higher illuminance must be employed. In other words, a light source lamp of a larger size must be employed. In this case, however, the diameter of the distal end of the inserting section becomes undesirably large. In addition, the distal end of the inserting section becomes hot due to heat generation, endangering the body portion under examination.

For the above reasons, it is difficult to increase the intensity of the illumination light in the conventional endoscope.

SUMMARY OF THE INVENTION

It is an object of the present invention to provide an endoscope capable of increasing the intensity of the illumination light without increasing the diameter of the inserting section or causing adverse effects due to heat generation, so that the object to be examined can be observed under sufficient light intensity.

An endoscope according to the present invention comprises a light source, an optical system provided at a distal end of an inserting section for guiding illumination light emitted from the light source onto an object, and means for moving a lens in the optical system along an optical axis thereof so as to vary the angle of view of the optical system.

BRIEF DESCRIPTION OF THE DRAWINGS

FIG. 1 is a block diagram of a configuration of an endoscope according to a first embodiment of the present invention;

FIGS. 2A to 2C show mechanisms for moving an illumination lens of the first embodiment along its optical axis;

FIG. 4 is a circuit diagram of an image enlargement controller according to the first embodiment of the present invention;

FIG. 6 is a block diagram of an endoscope according to a second embodiment of the present invention.

DETAILED DESCRIPTION OF THE PREFERRED EMBODIMENTS

Figure 3A:
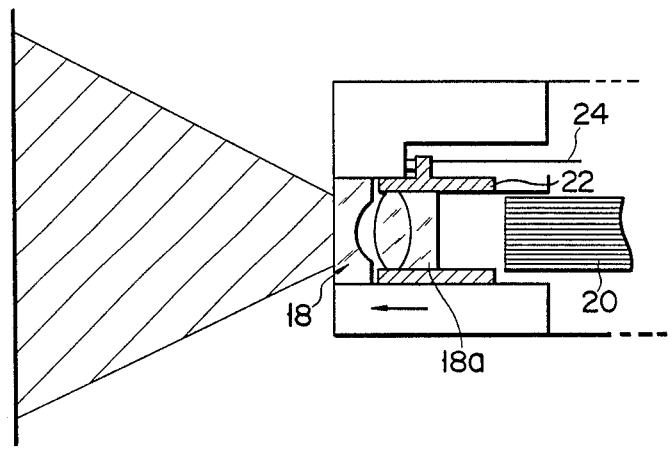
FIGS. 3A and 3B are views for explaining a change in the angle of view of the optical system when the illumination lens is moved along its optical axis.

An endoscope according to the first embodiment of the present invention will be described with reference to the accompanying drawings. FIG. 1 is a block diagram of a configuration of the first embodiment. This embodiment exemplifies an electronic scope system wherein a solid-state image pickup element is incorporated in the distal end of an endoscope. The system includes endoscope main body 10, light source unit 12, and CRT monitor 14. Illumination optical system 18 for illuminating an object 17 in the body cavity, and objective optical system 16 for obtaining an optical image of object 17 are provided in the distal end of main body 10. Illumination light from unit 12 is transmitted to optical system 18 via light guide 20 comprising an optical fiber bundle. A component of optical system 18, i.e., illumination lens 18a on the light guide 20 side, is mounted on frame 22 movable along the optical path of the illumination light. In other words, optical system 18 comprises a zoom lens. Frame 22 can be moved forward and backward by control section 11 of main body 10 through wire 24. An optical image of object 17 which is obtained by objective lens 16 is picked up by solid-state image pickup element (CCD in this case) 26.

Unit 12 has lamp 30 for emitting illumination light to be incident on light guide 20 in main body 10. The illumination light from lamp 30 is colored by rotating color filter 32 to have red (R), green (G), and blue (B) light components sequentially for every one frame image pickup period of CCD 26. Therefore, object 17 is colored R, G, and B sequentially in one frame image pickup period of CCD 26. CCD 26 picks up R, G, and B component images in one frame image pickup period to perform color image pickup in accordance with a sequential surface scheme. Filter 32 includes a filter disc having R, G, and B regions arranged sequentially along its circumference, and is rotated by motor 33 in synchronism with the image pickup operation by CCD 26. R, G, and B picture image signals from CCD 26 are sequentially input in video processor 34 in unit 12, are converted into parallel color image signals by video processor 34, and are supplied to image enlargement processor 36. Processor 36 enlarges and displays the image on monitor 14 when the focal length of optical system 18 is varied to narrow the angle of view. The details of processor 36 is shown in FIG. 4.

FIGS. 2A to 2C show mechanisms for moving frame 22 holding lens 18a along its optical path, i.e., a zoom mechanism of optical system 18. All of the mechanisms in FIGS. 2A to 2C move wire 24 to the right and left in the drawings. In FIG. 2A, teeth are provided on terminal member 42 of wire 24, and ring 40 engaged with the teeth is provided in control section 11 of main body 10. When ring 40 is rotated, the teeth of member 42 are engaged therewith, thereby moving wire 24 to the right or left. In FIG. 2B, rack 44 is connected to the end of wire 24. When pinion 46 in control section 11 is rotated, rack 44 and wire 24 can be moved to the right or left. Wire 24 can also be moved to the right or left by the rotational movement of lever 47 in accordance with a link mechanism shown in FIG. 2C.

Figure 3B:
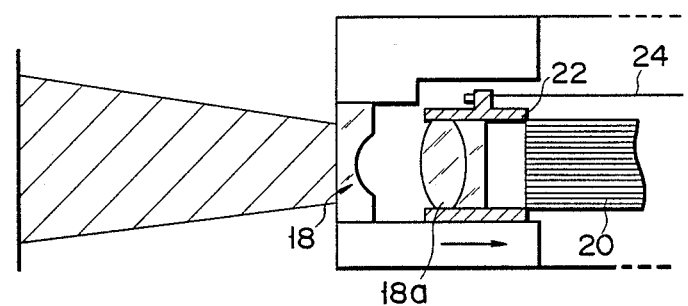

A change in the illumination range of lens 18a in a case where it is moved along its optical axis will be described. When lens 18a is moved forward, as shown in FIG. 3A, the focal length of optical system 18 is shortened, the angle of view thereof is widened, and the illumination range (the hatched region in the drawing) is also widened. Inversely, when lens 18a is moved backward, as shown in FIG. 3B, the focal length of optical system 18 is elongated, the angle of view thereof is narrowed, and the illumination range is narrowed as well. In this manner, when the illumination range is narrowed, the light intensity per unit area of the object is increased, even if the amount of light transmitted through light guide 20 is the same. When the object to be examined is smaller than the image-pickup range of CCD 26, the illumination range is narrowed as shown in FIG. 3B so that the light intensity per unit area of the object is increased.

FIG. 4 is a block diagram showing image enlargement processor 36 of FIG. 1 in detail. An output signal from CCD 26 is supplied to video processor 34 having sample/hold (SH) circuit 50, low pass filter (LPF) 52, and multiplexer 54. Multiplexer 54 switches an output from LPF 52 to one of three output terminals for every one frame. As described above, CCD 26 sequentially outputs R, G, and B image signals for every one frame. Multiplexer 54 outputs the R, G, and B image signals to the first, second and third output terminals. The first, second, and third output signals (R, G, and B signal components) from multiplexer 54 are written in frame memories 58a, 58b, and 58c via A/D converters 56a, 56b, and 56c, respectively. The image signals read out from frame memories 58a, 58b, and 58c are then written in frame memories 62a, 62b, and 62c via digital filters 60a, 60b, and 60c, respectively. Subsequently, the image signals read out from frame memories 62a, 62b, and 62c are supplied to CRT monitor 14 as the R, G, and B signal components via D/A converters 64a, 64b, and 64c, and analog filters 66a, 66b, and 66c, respectively. Timing controller 68 is connected to A/D converters 56a, 56b, and 56c, D/A converters 64a, 64b, and 64c, frame memories 58a, 58b, and 58c, and frame memories 62a, 62b, and 62c. A magnification data (Mg data) corresponding to the shifting amount of the moving mechanism of lens 18a is supplied to timing controller 68. "Magnification" used here means the ratio of the size of the entire display screen of CRT monitor 14 to the illumination range, which is reduced by movement of lens 18a as shown in FIG. 3B.

The operation of the first embodiment will be described. The operator directs the distal end of the inserting section of the main body 10 to the object 17. Note that an object to be examined does not always coincide with the size of the display screen. If the object to be examined occupies only part of the display screen, it is enlarged and displayed. In this case, the operator controls the angle of the distal end of the endoscope so that the object to be enlarged is located at the central portion of the display screen of CRT monitor 14. In this case, the illumination light covers the entire area of the image pickup range (image-pickup surface) of CCD 26. The operator moves lens 18a backward as shown in FIG. 3B, and narrows the angle of view of optical system 18, and thus the illumination range, so that the illumination light illuminates only the object to be enlarged. As a result, although the display screen of CRT monitor 14 excluding the object to be enlarged becomes dark, the light intensity on the object is increased. An image signal picked up under this condition is supplied to processor 36 through video processor 34, and is enlarged in the following manner.

Figure 5A:
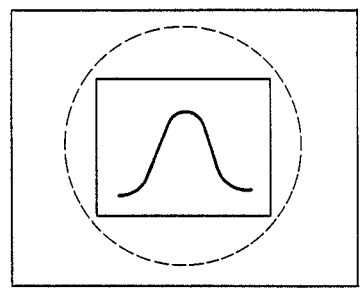
FIGS. 5A to 5C are views for explaining image enlargement processing.
Figure 5B:
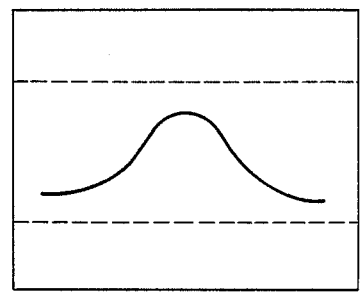

Timing controller 68 supplies an A/D conversion timing signal to A/D converters 56a, 56b, and 56c, and a write signal (WR) to frame memories 58a, 58b, and 58c in accordance with the magnification signal, and writes only a predetermined portion of the image signal output from CCD 26 in frame memories 58a, 58b, and 58c. This enlargement process is shown in FIGS. 5A and 5B. Assume that ¼ of the monitor screen at the central portion thereof is the object to be enlarged (object to be examined). As shown by a broken line in FIG. 5A, lens 18a is adjusted so that the circle around the object to be enlarged corresponds to the illumination range. In this example, the magnification signal is an enlargement magnification signal of x 2 in the vertical direction and x 2 in the horizontal direction. An image signal enlarged by x 2 in the horizontal direction as shown in FIG. 5B is written in frame memories 58a, 58b, and 58c. The broken lines in FIG. 5B define the horizontal x 2 enlarged region corresponding to the central portion in FIG. 5A.

Figure 5C:
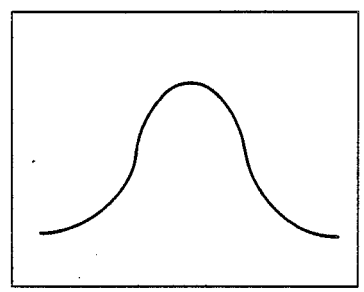

The part of image signals in frame memories 58a, 58b, and 58c which are defined by the broken lines in FIG. 5B are then transferred to frame memories 62a, 62b, and 62c. In this case, controller 68 supplies a read signal (RD) to frame memories 58a, 58b, and 58c, and a write signal (WR) to frame memories 62a, 62b, and 62c in accordance with the magnification signal, thereby changing the magnification of the image signals. Thereafter, the images in memories 58a, 58b, and 58c are enlarged by x 2 in the vertical direction, as shown in FIG. 5C. As a result, the image of the inner rectangular region of FIG. 5A read out from CCD 26 is enlarged in accordance with the magnification signal and is displayed on the entire surface of the display screen of CRT monitor 14.

As described above, according to the first embodiment of the present invention, the spot diameter of the illumination light is changed in accordance with the size of the object to be examined, which is displayed on the screen, so that the light intensity on the object can be increased. After image pickup, the object is enlarged to cover the entire surface of the display screen. Since the image is enlarged by signal processing using the frame memories, the configuration of the entire system can be simple and can easily cope with the change in the magnification.

FIG. 6 is a block diagram of a second embodiment of the present invention. The second embodiment is applied to a conventional fiber scope, not an electronic scope. More specifically, image guide 70 comprising an optical fiber bundle, like light guide 20 of the first embodiment, is provided in place of CCD 26. An optical image obtained by objective optical system 16 is transmitted to ocular 72 at the rear end of endoscope control section 11 via image guide 70. The object to be examined is observed by a human eye on the basis of the optical image transmitted to ocular 72. In this case, the size of the angle of view is changed in the same manner as in the first embodiment and the object to be examined can be observed with a constantly sufficient light intensity by changing the angle of view of the illumination light.

The present invention is not limited to the embodiments described above, and various modifications can be made within the spirit and scope of the invention. In the above embodiments, the light source is provided outside the endoscope main body. However, the present invention can be applied to an endoscope wherein a light source lamp is incorporated in the distal end of an inserting section. In this case, in the same manner as the embodiments described above, the illumination light from the light source lamp illuminates the object through an illumination optical system having a zoom lens. Further, the image enlargement processing in the electronic scope system is not limited to the first embodiment.

As described above, according to the present invention, the focal length of an illumination optical system provided on the distal end of the inserting section of the endoscope, i.e., an angle of view, is variable, and the illumination light illuminates only an object to be examined within the field of view. Therefore, the intensity of the illumination light can be increased without increasing the diameter of the inserting section or causing adverse effects due to heat generation, thereby providing an endoscope which can observe an object under sufficient light intensity.

What is claimed is:

1. An endoscope comprising:
   light source means;
   an objective optical system provided in the distal end of an inserting section of an endoscope main body and having a predetermined angle of view;
   an illumination optical system provided in the distal end of the inserting section of the endoscope main body for guiding illumination light from said light source means onto an object; and
   means for moving a lens of said illumination optical system along an optical axis thereof in order to vary an angle of view of said illumination system within the view field of the objective optical system.

2. An endoscope according to claim 1, in which said illumination optical system comprises a zoom lens wherein said lens thereof is supported by a frame movable along the optical axis thereof, and said view angle varying means comprises a wire with an end connected to said frame, and wire operating means, provided in a control section of said endoscope main body and connected to the other end of said wire, for moving said wire along the optical axis.

3. An endoscope according to claim 2, in which said wire operating means comprises a rotating ring, provided in said control section of said endoscope main body and having teeth on an inner surface thereof, and teeth connected to the other end of said wire to be engaged with said teeth on the inner surface of said ring.

4. An endoscope according to claim 2, in which said wire operating means comprises a rack provided in said control section of said endoscope main body, and a pinion connected to the other end of said wire to be engaged with said pinion.

5. An endoscope according to claim 2, in which said wire operating means comprises a reciprocal moving lever provided in said control section of said endoscope main body, and a link, connected to the other end of said wire, for transmitting reciprocal movement of said lever thereto.

6. An endoscope according to claim 1, which further comprises:
   image pickup means provided inside of said objective optical system; and
   image enlargement processing means for enlarging an image obtained by said image pickup means in accordance with the angle of view of said illumination optical system.

7. An endoscope according to claim 6, in which said image enlargement processing means comprises a first frame memory for receiving only a predetermined horizontal scanning line component of the image obtained by said image pickup means, the predetermined horizontal scanning line component corresponding to the angle of view of said illumination optical system, and enlarging the image in a horizontal direction, and a second frame memory for receiving only a predetermined component of each scanning line read out from said first frame memory, the predetermined component corresponding to the angle of view of said illumination optical system, and enlarging the image in a vertical direction.

8. An endoscope according to claim 1, in which said light source means is provided outside said endoscope main body and guides the illumination light to said illumination optical system via an optical fiber bundle in said endoscope main body.

9. An endoscope according to claim 1, which further comprises:
   image guide means formed of an optical fiber bundle for transmitting the image obtained by said objective optical system to the proximal end of the endoscope main body; and
   ocular means provided in the proximal end of the endoscope main body.

10. An endoscope comprising:
    solid state image pickup means provided in the distal end of an inserting section of an endoscope main body for picking up an object within a predetermined scope;
    an illumination optical system for illuminating an object with a light from a light source;
    view angle changing means for moving a lens of said illumination optical system along an optical axis thereof in order to vary an angle of view of said illumination optical system; and
    image enlargement processing means for enlarging a part of an image obtained by said solid image pickup means in response to change of the view angle of said illumination optical system, said part corresponding to the part illuminated by the illumination optical system.

11. An endoscope according to claim 10, in which said image enlargement processing means comprises a first frame memory for receiving only a predetermined horizontal scanning line component of the image obtained by said image pickup means, the predetermined horizontal scanning line component corresponding to the angle of view of said optical system, and enlarging the image in a horizontal direction, and a second frame memory for receiving only a predetermined component of each scanning line read out from said first frame memory, the predetermined component corresponding to the angle of the view of said optical system, and enlarging the image in a vertical direction.

* * * * *